United States Patent
Grenier et al.

(10) Patent No.: US 9,999,590 B2
(45) Date of Patent: Jun. 19, 2018

(54) DICLOFENAC FORMULATIONS

(71) Applicant: FERRING B.V., Hoofddorp (NI)

(72) Inventors: Arnaud Grenier, Steinbrunn le haut (FR); Dario N. Carrara, Oberwil (CH)

(73) Assignee: Ferring B.V., Hoofddorp (NL)

( * ) Notice: Subject to any disclaimer, the term of this patent is extended or adjusted under 35 U.S.C. 154(b) by 0 days. days.

(21) Appl. No.: 14/413,922

(22) PCT Filed: Jul. 4, 2013

(86) PCT No.: PCT/EP2013/064123
§ 371 (c)(1),
(2) Date: Jan. 9, 2015

(87) PCT Pub. No.: WO2014/009241
PCT Pub. Date: Jan. 16, 2014

(65) Prior Publication Data
US 2015/0297507 A1    Oct. 22, 2015

(30) Foreign Application Priority Data
Jul. 12, 2012    (EP) .................................... 12176115

(51) Int. Cl.
| A61K 9/70 | (2006.01) |
| A61K 9/00 | (2006.01) |
| A61K 47/10 | (2017.01) |
| A61K 31/196 | (2006.01) |
| A61K 45/06 | (2006.01) |

(52) U.S. Cl.
CPC ............ *A61K 9/0014* (2013.01); *A61K 9/006* (2013.01); *A61K 31/196* (2013.01); *A61K 45/06* (2013.01); *A61K 47/10* (2013.01)

(58) Field of Classification Search
CPC .... A61K 31/196; A61K 47/10; A61K 9/0014; A61K 2300/00; A61K 31/025; A61K 31/435
See application file for complete search history.

(56) References Cited

U.S. PATENT DOCUMENTS

| 6,509,040 | B1 | 1/2003 | Murray et al. |
| 6,911,217 | B1 | 6/2005 | Gren et al. |
| 7,335,379 | B2 | 2/2008 | Carrara et al. |
| 7,560,429 | B2 | 7/2009 | Nilsson et al. |
| 7,732,489 | B2 | 6/2010 | Steiger |
| 8,007,830 | B2 | 8/2011 | Down |
| 8,158,152 | B2 | 4/2012 | Palepu |
| 8,946,153 | B2 | 2/2015 | Gupta et al. |
| 9,096,335 | B2 | 8/2015 | Ahuja |
| 2004/0096569 | A1 | 5/2004 | Barkalow et al. |
| 2005/0266088 | A1 | 12/2005 | Hinrichs et al. |
| 2007/0225379 | A1* | 9/2007 | Carrara ................ A61K 9/7015 514/756 |
| 2008/0044900 | A1 | 2/2008 | Mooney et al. |
| 2009/0246257 | A1 | 10/2009 | Modi |
| 2012/0004306 | A1 | 1/2012 | Miura et al. |

FOREIGN PATENT DOCUMENTS

| EP | 2 055 298 | 5/2009 |
| JP | 2012-510439 | 5/2012 |
| WO | WO 2007/066148 A1 | 6/2007 |
| WO | WO 2008/005240 A2 | 1/2008 |
| WO | WO 2010/060798 A1 | 6/2010 |
| WO | WO 2010/103845 A1 | 9/2010 |

OTHER PUBLICATIONS

International Search Report, PCT/EP2013/064123, dated Jul. 30, 2013.

* cited by examiner

*Primary Examiner* — Nannette Holloman
(74) *Attorney, Agent, or Firm* — Finnegan, Henderson, Farabow, Garrett & Dunner, LLP (57) ABSTRACT

The subject invention provides improved diclofenac gel formulations.

33 Claims, 6 Drawing Sheets

DICLOFENAC FORMULATIONS

This is a national stage application under 35 U.S.C. § 371 of International Application No. PCT/EP2013/064123, filed Jul. 4, 2013, and claims priority to European Patent Application No. 12176115.9, filed Jul. 12, 2012, the content of each of which is incorporated herein by reference.

FIELD OF THE INVENTION

The subject invention lies in the field of transdermal diclofenac formulations.

BACKGROUND OF THE INVENTION

Delivery of active agents across the skin or mucosal membrane is convenient, pain-free, non-invasive and circumvents problems associated with the "first pass effect". Such transdermal or topical drug delivery is typically restricted to low molecular weight drugs and drugs with specific lipophilic/hydrophilic balance able to penetrate the stratum corneum.

Transdermal drug delivery systems enable chemical modification of the barrier properties of the skin to effectively and efficiently permit permeation thereof. Known drawbacks of transdermal delivery systems are, for example, the length of time needed for permeation, a frequent dosing regimen, and the volume size of a transdermal composition needed to transdermally deliver a sufficient therapeutic amount of the active agent.

Diclofenac (2-(2,6-dichloranilino) phenylacetic acid) is a non-steroidal anti-inflammatory drug (NSAID) used to reduce inflammation and, as an analgesic, to reduce pain. It is available in sodium, potassium, epolamine or diethylamine salt form in numerous dosage forms (oral tablet, oral syrup, topical gel, cataplasm, ophthalmic drop, suppository, etc.).

An example of a well-known transdermal diclofenac formulation is Voltaren® Gel 1% which comprises 1% diclofenac sodium. Voltaren® is indicated in the USA for the relief of the pain due to osteoarthritis of joints amenable to topical treatment, such as the knees and the hands. Up to 4 g of Voltaren® gel can be applied to lower extremities (including the knees, the ankles, and the feet) 4 times daily so that up to not more than 16 g daily of Voltaren® Gel 1% is applied to any single joint of the lower extremities. Up to 2 g of Voltaren® Gel 1% can also be applied to the upper extremities (which include the elbows, the wrists and the hands) 4 times daily so that up to not more than 8 g daily of Voltaren® Gel 1% is applied to any single joint of the upper extremities. Overall, the total dose of Voltaren® Gel 1% should not exceed 32 g per day over all affected joints. Neither the total amount (up to 32 g per day) nor the frequency of application (4 times a day) are satisfactory from a patient perspective.

U.S. Pat. No. 7,335,379 discloses formulations for transdermal or transmucosal administration of active agents, such as diclofenac, containing an alkanol, a polyalcohol, a monoalkyl ether of diethylene glycol and a fatty alcohol with a fatty alcohol content of up to 2%.

SUMMARY OF THE INVENTION

It is an object of the invention to provide improved diclofenac formulations with improved diclofenac delivery across the skin.

It is a further object of the invention to provide improved diclofenac formulations allowing a reduced frequency of administration.

It is a further object of the invention to provide improved diclofenac formulations to be used in the treatment of both localized and systemic conditions.

The subject invention provides a transdermal or transmucosal formulation comprising:
at least 3% wt of diclofenac,
$C_2$ to $C_4$ alkanol,
polyalcohol, and
monoalkyl ether of diethylene glycol; and
at least 3% wt of a fatty alcohol.

The subject invention further provides a transdermal or transmucosal formulation comprising: 3% wt of diclofenac, 45.0% wt of ethanol, 20.0% wt of propylene glycol, 5.0% wt of diethylene glycol monoethyl ether and 3% wt of myristyl alcohol.

The subject invention further provides a transdermal or transmucosal formulation comprising: 3% wt of diclofenac, 45.0% wt of ethanol, 20.0% wt of propylene glycol, 5.0% wt of diethylene glycol monoethyl ether, 3% wt of myristyl alcohol, 1.50% wt of hydroxypropyl cellulose, and water.

The subject invention further provides a method for administering diclofenac to a mammal in need thereof, said method comprising transdermally administering to the skin or a mucosal membrane of a mammal a formulation of the invention.

The subject invention further provides a method for treating pain; post-traumatic inflammation of tendons, ligaments, muscles and/or joints; localized forms of soft-tissue rheumatism; localized forms of degenerative rheumatism; inflammatory disorders; dysmenorrhea; actinic keratosis caused by over-exposure to sunlight; acute migraine; female breast cancer; pain associated with bony metastases; fever due to malignant lymphogranulomatosis (Hodgkin's lymphoma); multi drug resistant *E. coli*; Shy-Drager syndrome; and diabetes mellitus, said method comprising transdermally administering to the skin or a mucosal membrane of a mammal a formulation of the invention.

The subject invention further provides a kit comprising at least one container comprising a formulation of the invention, and instructions for use thereof.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

The subject invention provides a transdermal or transmucosal formulation comprising:
at least 3% wt of diclofenac,
$C_2$ to $C_4$ alkanol,
polyalcohol, and
monoalkyl ether of diethylene glycol; and
at least 3% wt of a fatty alcohol.

In one embodiment, the transdermal or transmucosal formulation further comprises at least one of a gelling agent, an anti-oxidant, and a solvent or any combination thereof.

It should be noted that the selection of the types and amounts of the components present in a formulation of the invention, other than diclofenac, is based on several factors, including, among others: potential for skin permeation of diclofenac from a formulation of the invention, ease of manufacturing, compatibility between the various components of a formulation of the invention, and stability of a formulation of the invention. It is furthermore noted that the components of the permeation enhancing system as defined herein are present in an amount sufficient to provide permeation enhancement of diclofenac through dermal or mucosal surfaces.

Unless expressly specified otherwise, the term "comprising" is used in the context of the present application to indicate that further members may optionally be present in addition to the members explicitly mentioned. It is, however, contemplated as a specific embodiment of the present invention that the term "comprising" encompasses the possibility of no members being present other than the ones explicitly mentioned. In other words, for the purpose of this specific embodiment, the term "comprising" is to be understood as having the meaning of "consisting of".

The following detailed description discloses specific and/or preferred variants of the individual features of the invention. The present invention also contemplates as encompassing, as particularly preferred embodiments of the invention, those embodiments which are obtained by combining two or more of the specific and/or preferred variants described for two or more of the features of the present invention.

Unless expressly specified otherwise, all indications of relative amounts in the present application are made on a weight/weight basis. Indications of relative amounts of a component characterized by a generic term are intended to refer to the total amount of all specific variants or members covered by said generic term. If a certain component defined by a generic term is specified to be present in a certain relative amount or range of amount, and if an embodiment of the invention further characterizes this component as comprising a specific variant or member covered by the generic term, it is intended that other variants or members covered by the generic term may be present only in an amount such that the total relative amount of all components covered by the generic term does not exceed the specified relative amount. Preferably, in such case, no other variants or members covered by the generic term are present at all.

Generally, when referring to a formulation comprising "x % wt" of an ingredient, such formulation should be understood to allow for a pharmaceutically acceptable variation in the % wt of said ingredient of ±10%. For example, when referring to a formulation comprising "3% wt of diclofenac", such formulation should be understood to allow for a pharmaceutically acceptable variation in the % wt of diclofenac of ±10%, i.e. from 2.7% wt to 3.3% wt.

The terms "transdermal formulation" or "transmucosal formulation" should be understood to encompass a formulation of the invention capable of delivering diclofenac to a mammal administered with said formulation by permeating the diclofenac through the skin or mucosal tissue (or membrane), said formulation being topically applied, penetrating into the target tissues (e.g. the synovial fluids of the joints), and eventually entering into the bloodstream of said mammal.

"Transdermal delivery" as used herein should be understood to encompass transdermal, percutaneous and transmucosal administration, i.e. delivery by passage/permeation of a drug through the skin or mucosal tissue into the bloodstream.

The term "skin" or "skin tissue" or "skin membrane" as used herein interchangeably should be understood to encompass any dermal membrane (including any epidermis or dermis layer of a skin membrane), including any hairy or glabrous cutaneous membrane.

The term "mucosa" or "mucosal tissue" or "mucosal membrane" as used herein interchangeably should be understood to encompass any moist anatomical membrane or surface on a mammal that can be permeated without swallowing such as oral, buccal, auricular, vaginal, rectal, nasal or ophthalmic surfaces.

The term "topical" or "topically" is used herein as referring to direct contact of a formulation of the invention with a surface area of a mammal, including any portion of a skin membrane or mucosal membrane.

The term "mammal" as used herein should be understood to encompass any mammal. In one embodiment, the mammal is a human.

When referring to diclofenac, it should be understood to refer to any one or more of the NSAID named 2-(2,6-dichloranilino) phenylacetic acid (CAS Registry Number 15307-86-5), its sodium salt, its potassium salt, its epolamine salt, its diethylamine salt, and/or any other pharmaceutically acceptable salt thereof.

For example, in one embodiment, a transdermal or transmucosal formulation of the invention comprises 3% wt of diclofenac, $C_2$ to $C_4$ alkanol, polyalcohol, monoalkyl ether of diethylene glycol and fatty alcohol. In another embodiment a transdermal or transmucosal formulation of the invention comprises 3% wt of diclofenac, $C_2$ to $C_4$ alkanol, polyalcohol, monoalkyl ether of diethylene glycol, fatty alcohol and gelling agent. In a further embodiment, a transdermal or transmucosal formulation of the invention comprises 3% wt of diclofenac, $C_2$ to $C_4$ alkanol, polyalcohol, monoalkyl ether of diethylene glycol, fatty alcohol, gelling agent, and anti-oxidant. In yet another embodiment, a transdermal or transmucosal formulation of the invention comprises 3% wt of diclofenac, $C_2$ to $C_4$ alkanol, polyalcohol, monoalkyl ether of diethylene glycol, fatty alcohol, gelling agent, anti-oxidant and solvent.

It is envisaged that a formulation of the invention comprises $C_2$-$C_4$ alkanol in an amount of about 5-60% wt (e.g. about 5, 10, 15, 20, 25, 30, 35, 40, 45, 50, 55, 60% wt), polyalcohol in an amount of about 1-30% wt (e.g. about 1, 2, 3, 4, 5, 10, 15, 20, 25, 30% wt), monoalkyl ether of diethylene glycol in an amount of about 0.2-25% wt (e.g. about 0.2, 0.3, 0.4, 0.5, 0.6, 0.7, 0.8, 0.9, 1.0, 2.0, 3.0, 4.0, 5.0, 6.0, 7.0, 8.0, 9.0, 10, 15, 20, 25% wt), and fatty alcohol in an amount of about 3-5% wt (e.g. 3.0, 3.5, 4.0, 4.5, 5.0% wt). A formulation of the invention may further optionally comprise, e.g., gelling agent(s) in an amount of about 0.05-5% wt (e.g. about 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5% wt) and/or anti-oxidant(s) in an amount of about 0.025-0.2% wt (e.g. about 0.025, 0.03, 0.035, 0.04, 0.045, 0.05, 0.055, 0.06, 0.065, 0.07, 0.075, 0.08, 0.085, 0.09, 0.095, 0.1%, 0.2% wt).

A "permeation enhancing system" as used herein should be understood to comprise $C_2$ to $C_4$ alkanol, polyalcohol, monoalkyl ether of diethylene glycol, and fatty alcohol, which together qualitatively and/or quantitatively enhance the absorption and/or permeation of diclofenac of a formulation of the invention through the skin or a mucosal membrane of a mammal treated with said formulation (as compared with the transdermal delivery of diclofenac without said permeation enhancing system).

The term "$C_2$ to $C_4$ alkanol" as used herein should be understood to mean one or more $C_2$ to $C_4$ alkanes substituted with a hydroxy group (—OH).

In one embodiment, an alkanol utilized by a formulation of the invention is one or more selected from the group consisting of ethanol, isopropanol, n-propanol, butan-1-ol and butan-2-ol. In another embodiment, said alkanol is ethanol. In a further embodiment, said alkanol is ethanol present in an amount of about 40.0-50.0% wt in a formulation of the invention. In a further embodiment, said alkanol is ethanol present in an amount of about 45.0% wt in a formulation of the invention.

In some embodiments, an alkanol (such as for example ethanol) is also utilized by a formulation of the invention as the primary solvent for the diclofenac. The quantity of the alkanol should be sufficient to at least fully solubilize the diclofenac. Additionally, alkanols, such as ethanol, are known to be efficient skin permeation enhancers which act by extracting polar stratum corneum lipids and, consequently, increase partitioning for numerous drug substances.

In some embodiments, a formulation of the invention comprises alkanol in a hydroalcoholic mixture with water.

In the context of the present invention, the term "polyalcohol" as used herein should be understood to mean one or more of a $C_2$ to $C_6$ alkane or $C_2$ to $C_6$ alkene, substituted with two or more hydroxy groups.

In some embodiments, a polyalcohol comprised in a formulation of the invention is one or more selected from the group consisting of ethylene glycol, propylene glycol, butylene glycol, and hexylene glycol. In one embodiment, a polyalcohol comprised in a formulation of the invention is propylene glycol. In another embodiment, a formulation of the invention comprises propylene glycol in an amount of about 20.0% wt.

The term "monoalkyl ether of diethylene glycol" as used herein should be understood to mean one or more diethylene glycols substituted with a $C_1$ to $C_6$ alkyl ether.

In one embodiment, monoalkyl ether of diethylene glycol comprised in a formulation of the invention is one or both of diethylene glycol monoethyl ether (DGME) and diethylene glycol monomethyl ether (DGMM). In another embodiment, a formulation of the invention comprises diethylene glycol monoethyl ether. In yet another embodiment, a formulation of the invention comprises diethylene glycol monoethyl ether in an amount of about 5.0% wt.

The term "fatty alcohol" as used herein should be understood to mean fatty alcohols having a branched or linear carbon body having 12 or more carbon atoms.

In one embodiment, the fatty alcohol comprised in a formulation of the invention is one or more selected from the group consisting of: myristyl alcohol, lauryl alcohol, oleyl alcohol, cetyl alcohol, and stearyl alcohol. In one embodiment, the fatty alcohol comprised in a formulation of the invention is myristyl alcohol. In another embodiment, a formulation of the invention comprises myristyl alcohol in an amount of about 3% wt. In yet another embodiment, a formulation of the invention comprises myristyl alcohol in an amount of more than about 3% wt. In yet another embodiment, a formulation of the invention comprises myristyl alcohol in an amount of about 3-5% wt.

In another embodiment, the formulation of the invention may comprise a fatty ester having a branched or linear acid moiety having 12 or more carbon atoms or having a branched or linear alcohol moiety having 12 or more carbon atoms.

The term "gelling agent" as used herein should be understood to mean any agent capable of transforming the composition into a gel. A gelling agent used in a formulation of the invention can be one or more selected from the group including: carbomer (also known as carboxyethylene or polyacrylic acid) such as carbomer (CARBOPOL™) 980NF or 940 NF, 981 or 941 NF, 1382 or 1342 NF, 5984 or 934 NF, ETD 2020, 934P NF, 971P NF, 974P NF, 71G NF, Ultrez 10 NF, Pemulen TR-1 NF or TR-2 NF and Noveon AA-1 USP, cellulose derivatives such as ethylcellulose (EC), hydroxypropylmethylcellulose (HPMC), ethylhydroxyethylcellulose (EHEC), carboxymethylcellulose (CMC), hydroxypropylcellulose (HPC) (Klucel different grades), hydroxyethylcellulose (HEC) (Natrosol grades), HPMCP 55, and Methocel grades, natural gums such as arabic, xanthan, guar gums, and alginates, polyvinylpyrrolidone derivatives such as Kollidon grades, polyoxyethylene-polyoxypropylene copolymers such as Lutrol F grades 68 and 127, chitosan, polyvinyl alcohols, pectins, and veegum grades. A tertiary amine, such as triethanolamine, trolamine, tromethamine, aminomethyl propanol, diisopropanolamine, or diethylamine, can be included to thicken and neutralize the system.

In one embodiment, the gelling agent comprised in a formulation of the invention is a carbomer. Carbomer relates to a class of homopolymers of acrylic acid with a high molecular weight, which are cross-linked with any of several polyalcohol allyl ethers. Non-limiting examples of carbomers are carbomer 940, carbomer 971P, carbomer 973, carbomer 974P, carbomer 980NF, and carbomer C981 NF (wherein the digit indicates the average molecular weight of the polymer chains).

In one embodiment, the gelling agent comprised in a formulation of the invention is hydroxypropylcellulose. In another embodiment, a formulation of the invention comprises hydroxypropylcellulose in an amount of about 1.50% wt.

The term "anti-oxidant" or "stabilizer" as used herein interchangeably should be understood to mean any substance capable of preventing oxidation or reactions promoted by oxygen, peroxides, or free radicals in a formulation. An anti-oxidant usable in a formulation of the invention can be one or more selected from the group including: tocopherol and derivatives, ascorbic acid and derivatives, butylated hydroxyanisole, butylated hydroxytoluene, fumaric acid, malic acid, citric acid, propyl gallate, sodium metabisulfite, sodium bisulfite, sodium sulfite, edetate disodium, edetate trisodium, edetate tetrasodium, and derivatives thereof. In one embodiment, the anti-oxidant comprised in a formulation of the invention is sodium metabisulfite. In another embodiment, the anti-oxidant comprised in a formulation of the invention is propyl gallate. In yet another embodiment, the anti-oxidant is edetate tetrasodium. In another embodiment, a formulation of the invention comprises sodium metabisulfite in an amount of from about 0.025% wt to about 0.10% wt. In yet another embodiment, a formulation of the invention comprises propyl gallate in an amount of up to about 0.05% wt. In yet another embodiment, a formulation of the invention comprises edetate tetrasodium in an amount of up to about 0.05% wt. In yet another embodiment, a formulation of the invention comprises sodium metabisulfite in an amount of from about 0.025% wt to about 0.10% wt and propyl gallate in an amount of up to about 0.05% wt. In yet another embodiment, a formulation of the invention comprises sodium metabisulfite in an amount of from about 0.025% wt to about 0.10% wt and edetate tetrasodium in an amount of up to about 0.05% wt.

As used herein the term "solvent" may encompass any type of solvent suitable for use in a transdermal or transmucosal formulation of the invention, as detailed herein above. In one embodiment, a solvent comprised in a formulation of the invention is water.

The subject invention provides a transdermal or transmucosal formulation comprising: 3% wt of diclofenac, 45.0% wt of ethanol, 20.0% wt of propylene glycol, 5.0% wt of diethylene glycol monoethyl ether and 3% wt of myristyl alcohol.

The subject invention further provides a transdermal or transmucosal formulation comprising: 3% wt of diclofenac, 45.0% wt of ethanol, 20.0% wt of propylene glycol, 5.0% wt of diethylene glycol monoethyl ether, 3% wt of myristyl alcohol, 1.50% wt of hydroxypropyl cellulose, and water.

The subject invention thus provides an advanced transdermal permeation enhancing system, comprising a combination of volatile solvent (e.g. ethanol) and non-volatile cosolvents (e.g. propylene glycol and e.g. diethylene glycol monoethyl ether) and fatty alcohols (e.g. myristyl alcohol), embedded in an aqueous gel matrix.

In some embodiments, a formulation of the invention further comprises at least one of a buffering agent, moisturizing agent, humectant, surfactant, neutralizing agent, chelating agent, emollient, or buffer.

In some embodiments, a formulation of the invention is in the form of a gel, lotion, cream, spray, aerosol, ointment, emulsion, suspension, liposomal system, lacquer, patch, bandage, buccal tablet, wafer, sublingual tablet, suppository, vaginal dosage form or occlusive dressing. In a particular embodiment, the formulation is a gel.

In other embodiments, a formulation of the invention is in the form of at least one of the following: a clear (transparent) formulation, a water washable formulation, a cool-to-the-touch formulation, a quick-drying formulation, a spreadable formulation and a non-greasy formulation.

In some embodiments, said formulation is in the form of a gel. In other embodiments, said formulation is in the form of a clear transparent gel.

In some embodiments, a formulation of the present invention is applied directly to the skin as, for example, a gel, an ointment, or a cream or indirectly through a patch, bandage, or other occlusive dressing.

A formulation of the invention may be applied once daily, or multiple times per day depending upon the condition of the patient. In some embodiments, said formulation is adapted for a once, twice, three times or four times daily transdermal or transmucosal administration.

The present invention further provides a method for administering diclofenac to a mammal in need thereof which comprises transdermally administering to the skin or a mucosal membrane of a mammal a formulation of the invention.

A formulation of the invention can be used for the treatment of both localized or systemic disorders. In that regard, the invention provides a transdermal or transmucosal formulation of the invention for use in the treatment of: pain (e.g. dental pain, mild to moderate post-operative or post-traumatic pain, mild to moderate post-operative or post-traumatic pain in presence of inflammation, menstrual pain, endometriosis, pain resulting from kidney stones and gallstones, chronic pain associated with cancer, chronic pain associated with cancer in presence of inflammation); post-traumatic inflammation of tendons, ligaments, muscles and/or joints (e.g. due to sprains, strains, and bruises); localized forms of soft-tissue rheumatism (e.g. tendovaginitis, bursitis, shoulder-hand syndrome, and periarthropathy); localized forms of degenerative rheumatism (e.g. osteoarthrosis of the peripheral joints of the vertebral column); inflammatory disorders (e.g. arthritis, rheumatoid arthritis, polymyositis, dermatomyositis, osteoarthritis, temporomandibular joint disorders, spondylarthritis, ankylosing spondylitis, and gout attacks); dysmenorrhea; actinic keratosis caused by over-exposure to sunlight; acute migraine; female breast cancer; pain associated with bony metastases; fever due to malignant lymphogranulomatosis (Hodgkin's lymphoma); multi drug resistant *E. coli*; Shy-Drager syndrome; and diabetes mellitus.

In one embodiment, the invention provides a transdermal or transmucosal formulation of the invention for use in the treatment of osteoarthritis.

A formulation of the invention can be administered in combination with other treatments.

In a further aspect, the invention provides a kit comprising at least one container comprising a formulation of the invention, and instructions for use thereof.

In some embodiments, a kit of the invention comprises a container which is adapted for dispensing a predetermined measured amount of said formulation.

EXAMPLES

The invention is further described in the following examples, which are not in any way intended to limit the scope of the inventions as claimed.

Example 1—Preparation of Diclofenac Gel Formulations

Figure 1:
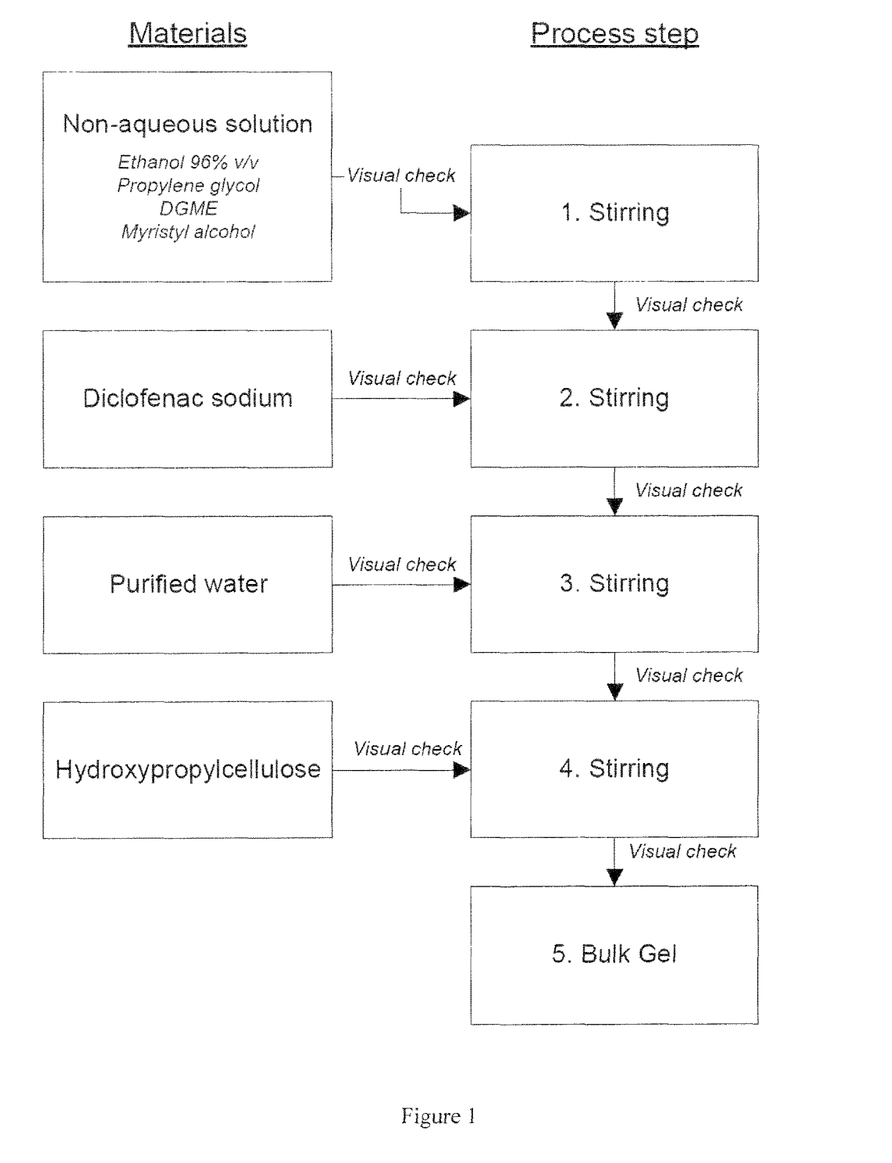
FIG. 1 shows a flow chart of the preparation of a diclofenac gel formulation of the invention.
Figure 2:
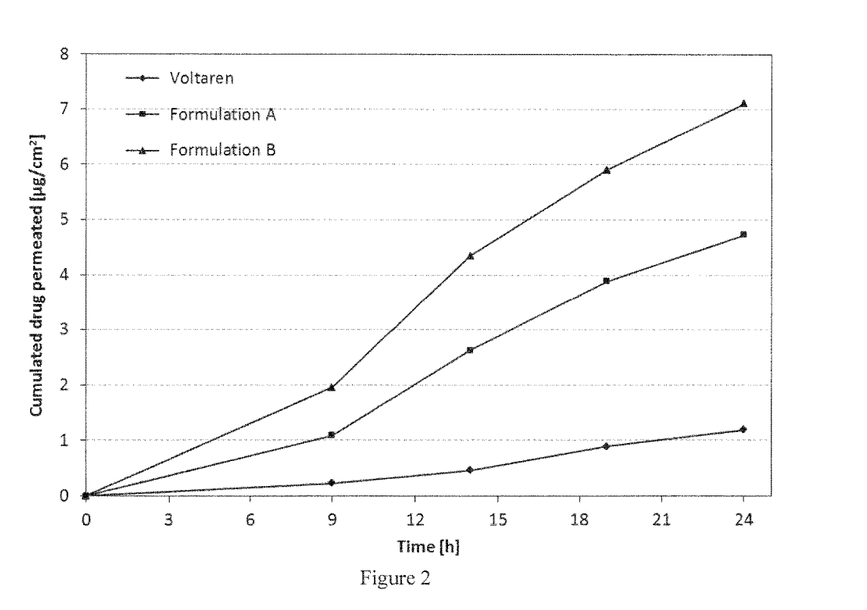
FIG. 2 shows the absolute permeation profile (in µg/cm$^2$) of Voltaren® and of diclofenac formulations A and B (see Example 2).
Figure 3:
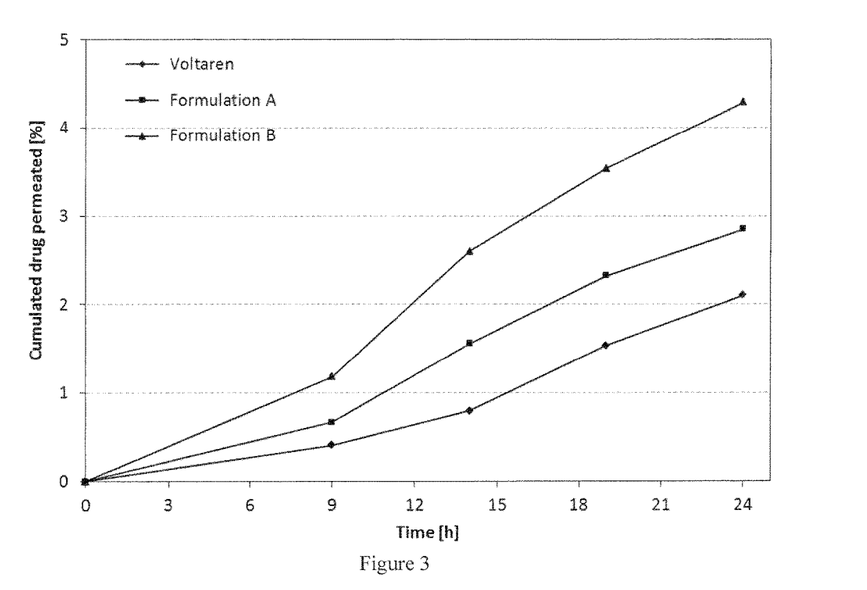
FIG. 3 shows the relative permeation profile (in %) of Voltaren® and of diclofenac formulations A and B (see Example 2).
Figure 4:
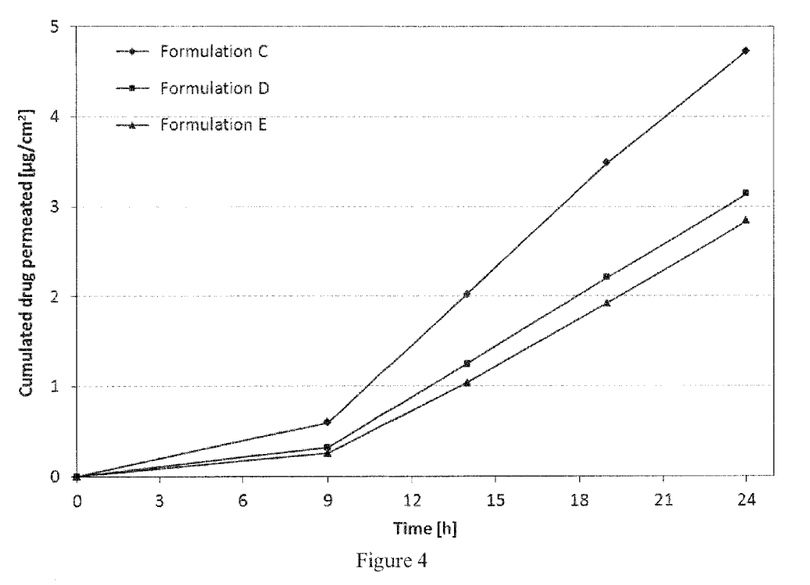
FIG. 4 shows the absolute permeation profile (in µg/cm$^2$) of diclofenac formulations C, D and E (see Example 3).
Figure 5:
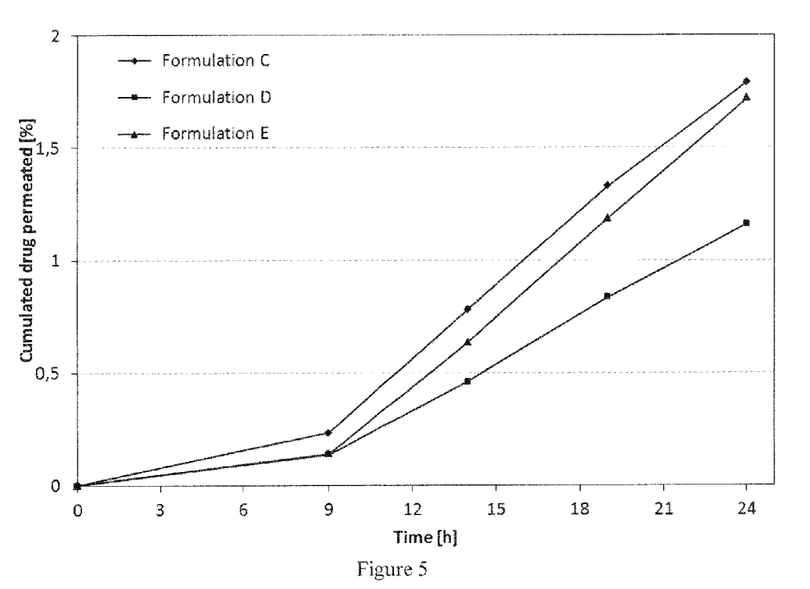
FIG. 5 shows the relative permeation profile (in %) of diclofenac formulations C, D and E (see Example 3).
Figure 6:
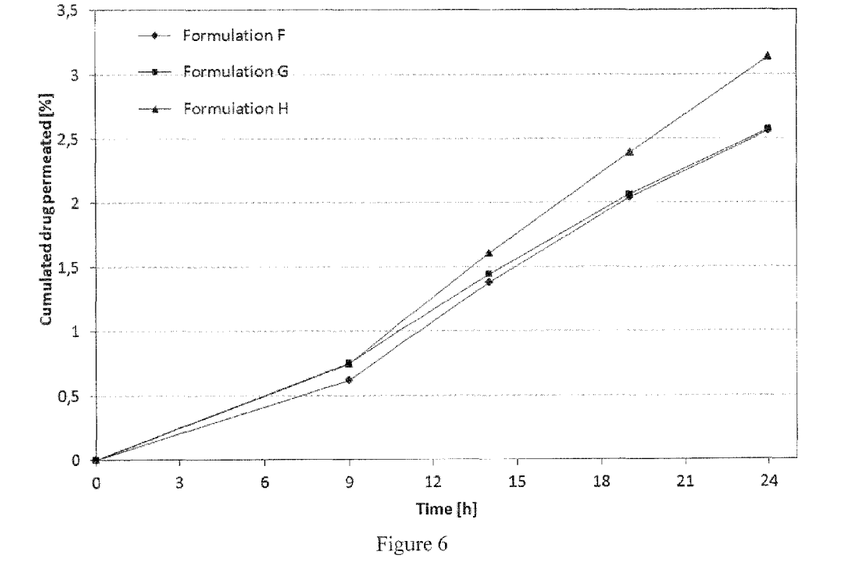
FIG. 6 shows the relative permeation profile (in %) of diclofenac formulations F, G and H (see Example 4).
Figure 7:
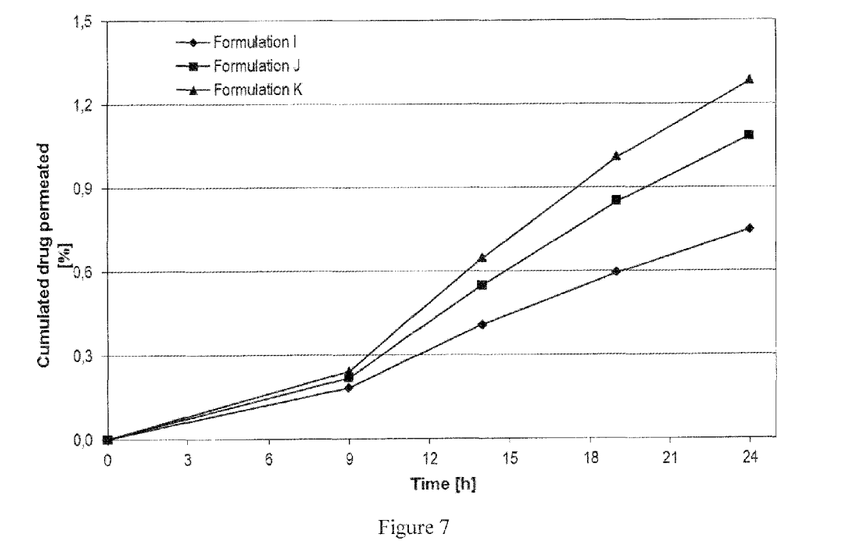
FIG. 7 shows the relative permeation profile (in %) of diclofenac formulations I, J and K (see Example 5).
Figure 8:
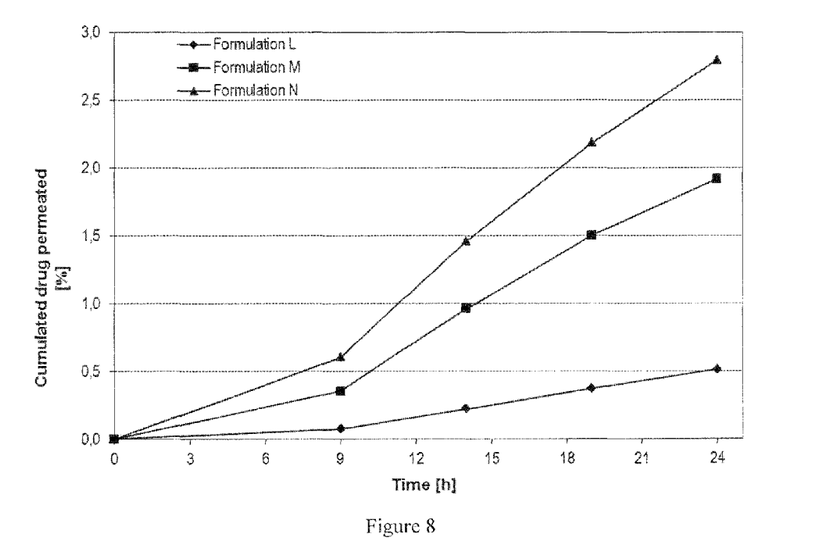
FIG. 8 shows the relative permeation profile (in %) of diclofenac formulations L, M and N (see Example 6).
Figure 9:
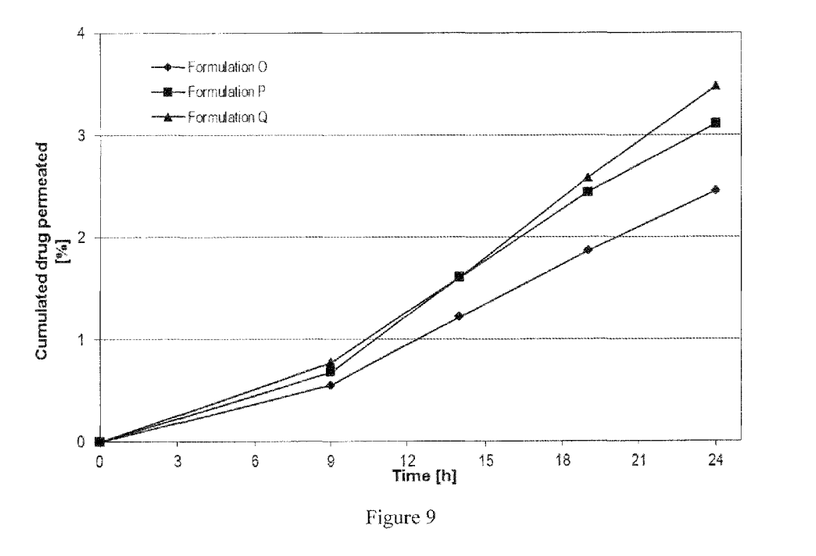
FIG. 9 shows the relative permeation profile (in %) of diclofenac formulations O, P and Q (see Example 7).
Figure 10:
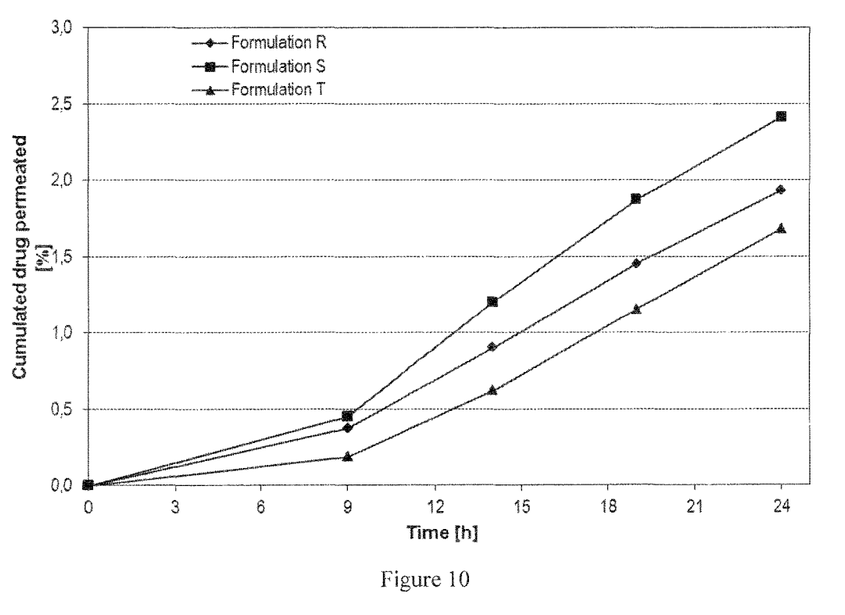
FIG. 10 shows the relative permeation profile (in %) of diclofenac formulations R, S and T (see Example 8).

The 3% wt and 5% wt diclofenac formulations described in the Examples below were prepared by methods known in the art, as schematically shown in FIG. 1. The preparation was carried out at bench scale (10 grams to 1000 grams batch sizes) in amber glass bottles. Mixing and homogenization was ensured either through magnetic stirring or by means of marine propellers. The preparation was also carried out at larger batch scale (e.g. 6 kg and beyond, e.g. 6-10 kg) in controlled environment under continuous vacuum and nitrogen blanketing with temperature control into a stainless steel planetary mixer.

Example 2—In Vitro Skin Permeation Testing

Test Samples:
Voltaren® Gel 1% wt
Diclofenac sodium gel 3% wt containing 2% wt myristyl alcohol (hereinafter Formulation A)

Diclofenac sodium gel 3% wt containing 3% wt myristyl alcohol (hereinafter Formulation B)

The composition of these gel formulations is presented in Tables 1 and 2.

TABLE 1

Voltaren ® Gel 1%

| COMPONENT | Function | % wt |
|---|---|---|
| Diclofenac sodium | Active | 1.00 |
| Carbomer homopolymer Type C | Thickener | ND |
| Cocoyl caprylocaprate (Cetiol LC) | Spreading emollient | ND |
| Isopropyl alcohol | Solvent | ND |
| Fragrance | Odour masking agent | ND |
| Mineral Oil (liquid paraffin) | Solvent | ND |
| Polyoxyl 20 cetostearyl ether | Consistency enhancer | ND |
| Propylene glycol | Solvent | ND |
| Strong ammonia solution | Neutralizing agent | ND |
| Water purified | solvent | qsf 100 |

ND = not disclosed in Voltaren ® leaflet.

TABLE 2

Formulations A and B

| COMPONENT | Function | A % wt | B % wt |
|---|---|---|---|
| Diclofenac sodium | Active | 3.0 | 3.0 |
| Absolute Ethanol | Solvent/skin permeation enhancer | 45.0 | 45.0 |
| Propylene glycol | Solvent/skin permeation enhancer | 20.0 | 20.0 |
| Diethylene glycol monoethyl ether | Solvent/skin permeation enhancer | 5.0 | 5.0 |
| Myristyl alcohol | Skin permeation enhancer | 2.0 | 3.0 |
| Hydroxypropylcellulose | Gelling agent (Thickener) | 1.50 | 1.50 |
| Purified water | Solvent | qs 100 | qs 100 |

Testing was performed on frozen abdominal human skin (from one single donor). The Voltaren® test formulation was tested in 4 replicates and the Diclofenac test formulations were tested each in 5 replicates (total 14 replicates, i.e. sliced skin samples). The thickness of each sample was measured with a micrometer. The samples were consequently mounted on vertical glass Franz diffusion cells with a receptor compartment of about 7.0 mL, a donor compartment of 3.0 mL and a diffusion area of 1.77 cm$^2$.

Phosphate buffered saline (PBS) with addition of 2% w/v oleth-20, i.e. polyoxyethylene (20) oleyl ether, at pH 7.4 was used as receptor solution, maintained at 32.5° C. during the whole study and stirred at 600 rpm. The study was performed using a Microette®Plus autosampler.

After 2 hours pre-incubation of the skin samples with the receptor solution and integrity assessment by evaporimetry, about 10 mg of the diclofenac sodium gel formulations were applied with the tip of a plastic syringe plunger and gently spread over the 1.77 cm$^2$ diffusion surface (thus reaching gel loading of 5.6 mg/cm$^2$). Diffusion of the drug was allowed in non-occluded conditions during 24 hours.

Receptor solution samples (1.0 mL) were automatically removed after 9 hours, 14 hours, 19 hours and 24 hours (after 1.5 mL receptor compartment priming). The samples were collected in 2 mL HPLC amber glass vials pre-sealed with septum crimp caps and pre-filled with 10 µL of a solution of trifluoroacetic (TFA) acid 10%. Then samples were transferred into Eppendorf microtubes and centrifuged at 13500 rpm during 5 minutes. Each supernatant (0.8 mL) was transferred in a 2 mL HPLC amber glass vial. Analysis of the samples was performed by HPLC.

The entire study was conducted at controlled room temperature (typically between 20° C. and 25° C.

TABLE 3

Diclofenac Cumulative delivery after 24 hour permeation

| Formulation | Replicates | Mean absolute delivery [µg/cm$^2$ ± SD] | Mean relative delivery [% ± SD] | Steady-state flux [µg/cm$^2$h] |
|---|---|---|---|---|
| Voltaren ® | 4 | 1.19 ± 0.82 | 2.1 ± 1.41 | 0.06 ± 0.05 |
| A | 5 | 4.73 ± 3.45 | 2.85 ± 1.99 | 0.21 ± 0.12 |
| B | 5 | 7.11 ± 2.27 | 4.29 ± 1.32 | 0.27 ± 0.10 |

Conclusion

Increasing the myristyl alcohol content in a 3% wt diclofenac sodium gel formulation from 2% wt to 3% wt (i.e. a 50% increase) led to a linear 1.5-fold increase of mean cumulative diclofenac delivery after 24 hours (from 4.7 µg/cm$^2$ to 7.1 µg/cm$^2$ in absolute, or from 2.9% to 4.3% in relative).

Example 3—In Vitro Skin Permeation Testing

Test Samples:
Diclofenac sodium gel 5% wt containing 3% wt myristyl alcohol (hereinafter Formulation C)

Diclofenac sodium gel 5% wt containing 2% wt myristyl alcohol (hereinafter Formulation D)

Diclofenac sodium gel 3% wt containing 2% wt myristyl alcohol (hereinafter Formulation E).

The composition of these gel formulations is presented in Table 4.

TABLE 4

Formulations C, D, and E

| COMPONENT | Function | C % wt | D % wt | E % wt |
|---|---|---|---|---|
| Diclofenac Sodium | Active | 5.0 | 5.0 | 3.0 |
| Absolute Ethanol | Solvent/skin permeation enhancer | 45.0 | 45.0 | 45.0 |
| Propylene glycol | Solvent/skin permeation enhancer | 20.0 | 20.0 | 20.0 |
| Diethylene glycol monoethyl ether | Solvent/skin permeation enhancer | 5.0 | 5.0 | 5.0 |
| Myristyl alcohol | Skin permeation enhancer | 3.0 | 2.0 | 2.0 |
| Hydroxypropylcellulose | Gelling agent (Thickener) | 1.5 | 1.5 | 1.5 |
| Purified water | Solvent | qs 100 | qs 100 | qs 100 |

Each test formulation was tested (essentially as described in Example 2) in six (6) replicates (6 different fresh pig ear skin donors). Overall, eighteen (18) full thickness samples were used.

TABLE 5

Diclofenac Cumulative delivery after 24 hour permeation

| Formulation | Replicates | Mean absolute delivery [µg/cm² ± SD] | Mean relative delivery [% ± SD] | Steady-state flux [µg/cm²h] |
|---|---|---|---|---|
| C | 6 | 4.73 ± 3.82 | 1.79 ± 1.43 | 0.25 ± 0.17 |
| D | 6 | 3.14 ± 1.92 | 1.16 ± 0.70 | 0.18 ± 0.08 |
| E | 6 | 2.84 ± 1.52 | 1.72 ± 0.89 | 0.17 ± 0.08 |

Conclusion

In a diclofenac 5% gel formulation, increasing the myristyl alcohol content from 2% to 3% (i.e. a 50% increase) led also to a linear 1.5-fold increase of mean cumulative diclofenac delivered through the skin after 24 hours (from 3.1 µg/cm² to 4.7 µg/cm² in absolute, or from 1.2% to 1.8% in relative).

Example 4—In Vitro Skin Permeation Testing

Test Samples:
  Diclofenac sodium gel 3% wt containing 3% wt myristyl alcohol (hereinafter formulation F)
  Diclofenac potassium gel 3.15% wt (equivalent to diclofenac sodium 3% wt) containing 3% wt myristyl alcohol (hereinafter formulation G)
  Diclofenac epolamine gel 3.88% wt (equivalent to diclofenac sodium 3% wt) containing 3% wt myristyl alcohol (hereinafter formulation H).
  The composition of these gel formulations is presented in Table 6.

TABLE 6

Formulations F, G and H

| COMPONENT | Function | F % wt | G % wt | H % wt |
|---|---|---|---|---|
| Diclofenac | Active | 3.0 | 3.15 | 3.88 |
| Absolute Ethanol | Solvent/skin permeation enhancer | 45.0 | 45.0 | 45.0 |
| Propylene glycol | Solvent/skin permeation enhancer | 20.0 | 20.0 | 20.0 |
| Diethylene glycol monoethyl ether | Solvent/skin permeation enhancer | 5.0 | 5.0 | 5.0 |
| Myristyl alcohol | Skin permeation enhancer | 3.0 | 3.0 | 3.0 |
| Hydroxy-propylcellulose | Gelling agent (Thickener) | 1.5 | 1.5 | 1.5 |
| Purified water | Solvent | qs 100 | qs 100 | qs 100 |

Each test formulation was tested (essentially as described in Example 2) in six (6) replicates (6 different fresh pig ear skin donors). Overall, eighteen (18) full thickness samples were used.

TABLE 7

Diclofenac Cumulative delivery after 24 hour permeation

| Formulation | Replicates | Mean absolute delivery [µg/cm² ± SD] | Mean relative delivery [% ± SD] | Steady-state flux [µg/cm²h] |
|---|---|---|---|---|
| F | 6 | 3.39 ± 1.91 | 2.07 ± 1.29 | 0.15 ± 0.07 |
| G | 6 | 3.25 ± 0.72 | 1.99 ± 0.48 | 0.14 ± 0.04 |
| H | 6 | 5.18 ± 2.62 | 3.20 ± 1.59 | 0.25 ± 0.102 |

Each test formulation was again tested (essentially as described in Example 2) in six (6) replicates (6 different fresh pig ear skin donors). Overall, eighteen (18) full thickness samples were used.

TABLE 8

Diclofenac Cumulative delivery after 24 hour permeation

| Formulation | Replicates | Mean absolute delivery [µg/cm² ± SD] | Mean relative delivery [% ± SD] | Steady-state flux [µg/cm²h] |
|---|---|---|---|---|
| F | 6 | 5.03 ± 3.56 | 3.05 ± 2.17 | 0.24 ± 0.15 |
| G | 6 | 3.44 ± 1.97 | 2.01 ± 1.12 | 0.18 ± 0.10 |
| H | 6 | 5.08 ± 4.33 | 3.06 ± 2.46 | 0.25 ± 0.13 |

TABLE 9

Compilation of Tables 7 and 8

| Formulation | Replicates | Mean relative delivery [% ± SD] |
|---|---|---|
| F | 12 | 2.56 ± 1.78 |
| G | 12 | 2.57 ± 2.15 |
| H | 12 | 3.13 ± 1.98 |

Conclusion

Use of any one of three salts of diclofenac, i.e. diclofenac sodium, diclofenac potassium and diclofenac epolamine in the presence of 3% wt myristyl alcohol resulted in similar diclofenac delivery through the skin after 24 hours.

Example 5—In Vitro Skin Permeation Testing

Test Samples:
  Diclofenac sodium gel 3% wt containing 3% wt myristyl alcohol (hereinafter formulation I)
  Diclofenac sodium gel 3% wt containing 3% wt myristyl alcohol and 0.1% sodium metabisulfite (hereinafter formulation J)
  Diclofenac sodium gel 3% wt containing 3% wt myristyl alcohol, 0.05% metabisulfite and 0.05% propyl gallate (hereinafter formulation K).
  The composition of these gel formulations is presented in Table 10.

TABLE 10

Formulations I, J and K

| COMPONENT | Function | I % wt | J % wt | K % wt |
|---|---|---|---|---|
| Diclofenac | Active | 3.0 | 3.0 | 3.0 |
| Absolute Ethanol | Solvent/skin permeation enhancer | 45.0 | 45.0 | 45.0 |
| Propylene glycol | Solvent/skin permeation enhancer | 20.0 | 20.0 | 20.0 |
| Diethylene glycol monoethyl ether | Solvent/skin permeation enhancer | 5.0 | 5.0 | 5.0 |
| Myristyl alcohol | Skin permeation enhancer | 3.0 | 3.0 | 3.0 |
| Hydroxy-propylcellulose | Gelling agent (Thickener) | 1.5 | 1.5 | 1.5 |
| Sodium metabisulfite | Anti-oxidant | — | 0.1 | 0.05 |
| Propyl gallate | Anti-oxidant | — | — | 0.05 |
| Purified water | Solvent | qs 100 | qs 100 | qs 100 |

Each test formulation was again tested (essentially as described in Example 2) in six (6) replicates (6 different fresh pig ear skin donors). Overall, eighteen (18) full thickness samples were used.

TABLE 11

Diclofenac Cumulative delivery after 24 hour permeation

| Formulation | Replicates | Mean absolute delivery [µg/cm² ± SD] | Mean relative delivery [% ± SD] | Steady-state flux [µg/cm²h] |
|---|---|---|---|---|
| I | 6 | 1.19 ± 0.53 | 0.75 ± 0.34 | 0.05 ± 0.02 |
| J | 6 | 1.77 ± 0.72 | 1.08 ± 0.46 | 0.09 ± 0.04 |
| K | 6 | 2.07 ± 1.96 | 1.28 ± 1.22 | 0.10 ± 0.09 |

Conclusion 0.1% sodium metabisulfite increases diclofenac delivery from 1.19 µg/cm² to 1.77 µg/cm²; a combination of 0.05% sodium metabisulfite and 0.05% propyl gallate increased diclofenac delivery to 2.07 µg/cm².

Thus, in the presence of anti-oxidant, diclofenac delivery is at least equivalent to the delivery without anti-oxidant and even improved.

Example 6—In Vitro Skin Permeation Testing

Test Samples:
Diclofenac potassium gel 3.15% wt, equivalent to diclofenac sodium 3% wt (hereinafter formulation L)
Diclofenac potassium gel 3.15% wt containing 2% wt myristyl alcohol (hereinafter formulation M)
Diclofenac potassium gel 3.15% wt containing 3% wt myristyl alcohol (hereinafter formulation N).

The composition of these gel formulations is presented in Table 12.

TABLE 12

Formulations L, M and N

| COMPONENT | Function | L % wt | M % wt | N % wt |
|---|---|---|---|---|
| Diclofenac | Active | 3.15 | 3.15 | 3.15 |
| Absolute Ethanol | Solvent/skin permeation enhancer | 45.0 | 45.0 | 45.0 |
| Propylene glycol | Solvent/skin permeation enhancer | 20.0 | 20.0 | 20.0 |
| Diethylene glycol monoethyl ether | Solvent/skin permeation enhancer | 5.0 | 5.0 | 5.0 |
| Myristyl alcohol | Skin permeation enhancer | — | 2.0 | 3.0 |
| Hydroxy-propylcellulose | Gelling agent (Thickener) | 1.5 | 1.5 | 1.5 |
| Purified water | Solvent | qs 100 | qs 100 | qs 100 |

Each test formulation was tested (essentially as described in Example 2) in six (6) replicates (6 different fresh pig ear skin donors). Overall, eighteen (18) full thickness samples were used.

TABLE 13

Diclofenac Cumulative delivery after 24 hour permeation

| Formulation | Replicates | Mean absolute delivery [µg/cm² ± SD] | Mean relative delivery [% ± SD] | Steady-state flux [µg/cm²h] |
|---|---|---|---|---|
| L | 6 | 0.83 ± 0.65 | 0.51 ± 0.41 | 0.05 ± 0.04 |
| M | 5 | 3.11 ± 1.45 | 1.92 ± 0.96 | 0.16 ± 0.05 |
| N | 6 | 4.7 ± 3.85 | 2.79 ± 2.23 | 0.22 ± 0.17 |

Conclusion

Formulation N, containing 3.15% diclofenac potassium together with 3% myristyl alcohol, had significantly higher diclofenac delivery.

Example 7—In Vitro Skin Permeation Testing

Test Samples:
Diclofenac sodium gel 3% wt containing 2.7% wt. myristyl alcohol (hereinafter formulation O)
Diclofenac sodium gel 3% wt containing 3% wt myristyl alcohol (hereinafter formulation P)
Diclofenac sodium gel 3% wt containing 3.3% wt myristyl alcohol (hereinafter formulation Q).

The composition of these gel formulations is presented in Table 14.

TABLE 14

Formulations O, P and Q

| COMPONENT | Function | O % wt | P % wt | Q % wt |
|---|---|---|---|---|
| Diclofenac | Active | 3.0 | 3.0 | 3.0 |
| Absolute Ethanol | Solvent/skin permeation enhancer | 40.5 | 45.0 | 49.5 |
| Propylene glycol | Solvent/skin permeation enhancer | 18.0 | 20.0 | 22.0 |
| Diethylene glycol monoethyl ether | Solvent/skin permeation enhancer | 4.5 | 5.0 | 5.5 |
| Myristyl alcohol | Skin permeation enhancer | 2.7 | 3.0 | 3.3 |
| Hydroxy-propylcellulose | Gelling agent (Thickener) | 1.5 | 1.5 | 1.5 |
| Purified water | Solvent | qs 100 | qs 100 | qs 100 |

Each test formulation was tested (essentially as described in Example 2) in six (6) replicates (6 different fresh pig ear skin donors). Overall, eighteen (18) full thickness samples were used.

TABLE 15

Diclofenac Cumulative delivery after 24 hour permeation

| Formulation | Replicates | Mean absolute delivery [µg/cm² ± SD] | Mean relative delivery [% ± SD] | Steady-state flux [µg/cm²h] |
|---|---|---|---|---|
| O | 6 | 4.16 ± 2.73 | 2.46 ± 1.6 | 0.21 ± 0.12 |
| P | 6 | 5.01 ± 4.67 | 3.11 ± 2.93 | 0.24 ± 0.18 |
| Q | 6 | 5.60 ± 2.92 | 3.48 ± 1.81 | 0.29 ± 0.14 |

Conclusion

Formulation O which contains 90% of target amounts of ethanol, propylene glycol, diethylene glycol monoethyl ether and myristyl alcohol, led to a statistically insignificant decrease of cumulated diclofenac through the skin after 24 hours (from 3.11% to 2.46%).

Similarly, formulation Q which contained 110% of target amounts of ethanol, propylene glycol, diethylene glycol monoethyl ether and myristyl alcohol, led to a statistically insignificant increase of cumulated diclofenac through the skin after 24 hours (from 3.11% to 3.48%).

Similar observation were also made with respect to the steady state flux which for formulation O led to a statistically insignificant decrease from 0.24 µg/cm²h to 0.21 µg/cm²h and for formulation Q led to a statistically insignificant increase from 0.24 µg/cm²h to 0.29 µg/cm²h.

Thus, variations within ±10% have a very limited impact on the permeability of diclofenac through the skin.

Example 8—In Vitro Skin Permeation Testing

Test Samples:
  Diclofenac sodium gel 3% wt containing 3% wt myristyl alcohol and 1.35% hydroxypropyl cellulose (equivalent to 7967 cP) (hereinafter formulation R)
  Diclofenac sodium gel 3% wt containing 3% wt myristyl alcohol and 1.5% hydroxypropyl cellulose (equivalent to 10617 cP) (hereinafter formulation S)
  Diclofenac sodium gel 3% wt containing 3% wt myristyl alcohol and 1.65% hydroxypropyl cellulose (equivalent to 13817 cP) (hereinafter formulation T).

The composition of these gel formulations is presented in Table 16.

TABLE 16

Formulations R, S and T

| COMPONENT | Function | R % wt | S % wt | T % wt |
|---|---|---|---|---|
| Diclofenac | Active | 3.0 | 3.0 | 3.0 |
| Absolute Ethanol | Solvent/skin permeation enhancer | 45.0 | 45.0 | 45.0 |
| Propylene glycol | Solvent/skin permeation enhancer | 20.0 | 20.0 | 20.0 |
| Diethylene glycol monoethyl ether | Solvent/skin permeation enhancer | 5.0 | 5.0 | 5.0 |
| Myristyl alcohol | Skin permeation enhancer | — | 2.0 | 3.0 |
| Hydroxypropylcellulose | Gelling agent (Thickener) | 1.35 | 1.5 | 1.65 |
| Purified water | Solvent | qs 100 | qs 100 | qs 100 |

Each test formulation was tested (essentially as described in Example 2) in six (6) replicates (6 different fresh pig ear skin donors). Overall, eighteen (18) full thickness samples were used.

TABLE 17

Diclofenac Cumulative delivery after 24 hour permeation

| Formulation | Replicates | Mean absolute delivery [µg/cm² ± SD] | Mean relative delivery [% ± SD] | Steady-state flux [µg/cm²h] |
|---|---|---|---|---|
| R | 6 | 3.21 ± 1.63 | 1.93 ± 1.06 | 0.16 ± 0.08 |
| S | 5 | 3.88 ± 1.19 | 2.41 ± 0.72 | 0.19 ± 0.04 |
| T | 52 | 4.7 ± 0.59 | 1.68 ± 0.35 | 0.17 ± 0.02 |

Conclusion

The increase of viscosity from about 8000 cP (formulation R) to about 14000 cP (formulation T) leads to a variation of diclofenac delivery of not more than 15% and of less than 10% of the steady-state flux.

Optimal delivery of diclofenac occurred at about 10000 cP.

The invention claimed is:

1. A transdermal or transmucosal formulation comprising:
at least 3% wt of diclofenac,
C2 to C4 alkanol,
polyalcohol, and
monoalkyl ether of diethylene glycol; and
an amount of about 3% wt-5% wt of a fatty alcohol.

2. The transdermal or transmucosal formulation according to claim 1, further comprising at least one of a gelling agent, an anti-oxidant, a solvent, and any combinations thereof.

3. The formulation of claim 2, wherein the alkanol is present in an amount of about 5-60% wt, the polyalcohol is present in an amount of about 1-30% wt, the monoalkyl ether of diethylene glycol is present in an amount of about 0.2-25% wt, the fatty alcohol is present in an amount of about 3-5% wt, the gelling agent is present in an amount of about 0.05-5% wt, and the anti-oxidant is present in an amount of about 0.025-2.0% wt.

4. The formulation of claim 1, wherein the alkanol is chosen from ethanol, isopropanol, n-propanol, butan-l-ol, and butan-2-ol.

5. The formulation of claim 4, wherein the alkanol is ethanol.

6. The formulation of claim 5, wherein the ethanol is present in an amount of about 45.0% wt.

7. The formulation of claim 1, wherein the polyalcohol is chosen from glycol, propylene glycol, butylene glycol, and hexylene glycol.

8. The formulation of claim 7, wherein the polyalcohol is propylene glycol.

9. The formulation of claim 8, wherein propylene glycol is present in an amount of about 20.0% wt.

10. The formulation of claim 1, wherein one or both of diethylene glycol monoethyl ether and diethylene glycol monomethyl ether are present as the monoalkyl ether of diethylene glycol.

11. The formulation of claim 10, wherein diethylene glycol monoethyl ether is present in an amount of 5.0% wt.

12. The formulation of claim 1, wherein the fatty alcohol is chosen from myristyl alcohol, lauryl alcohol, oleyl alcohol, cetyl alcohol, and stearyl alcohol.

13. The formulation of claim 12, wherein the fatty alcohol is myristyl alcohol.

14. The formulation of claim 2, wherein the gelling agent is hydroxypropyl cellulose.

15. The formulation of claim 14, wherein the hydroxypropyl cellulose is present in an amount of 1.50% wt.

16. The formulation of claim 2, wherein the anti-oxidant is sodium metabisulfite, propyl gallate, edetate tetrasodium, or a combination thereof.

17. The formulation of claim 16, wherein the anti-oxidant is sodium metabisulfite in an amount of about 0.025 to 0.10% wt.

18. The formulation of claim 16, wherein the anti-oxidant is propyl gallate in an amount of up to about 0.05% wt.

19. The formulation of claim 16, wherein the anti-oxidant is edetate tetrasodium in an amount of up to about 0.05% wt.

20. The formulation of claim 16, wherein the anti-oxidant is sodium metabisulfite in an amount of about 0.025 to 0.10% wt together with propyl gallate in an amount of up to about 0.05% wt.

21. The formulation of claim 16, wherein the anti-oxidant is sodium metabisulfite in an amount of about 0.025 to 0.10% wt together with edetate tetrasodium in an amount of up to about 0.05% wt.

22. The formulation of claim 2, wherein the solvent is water.

23. The transdermal or transmucosal formulation of claim 1 comprising: 3% wt of diclofenac, 45.0% wt of ethanol, 20.0% wt of propylene glycol, 5.0% wt of diethylene glycol monoethyl ether, and 3% wt of myristyl alcohol.

24. The transdermal or transmucosal formulation of claim 1 comprising: 3% wt of diclofenac, 45.0% wt of ethanol, 20.0% wt of propylene glycol, 5.0% wt of diethylene glycol monoethyl ether, 3% wt of myristyl alcohol, 1.50% wt of hydroxypropyl cellulose, and water.

25. The formulation of claim 1, wherein said formulation is in the form of a gel, lotion, cream, spray, aerosol, ointment, emulsion, suspension, liposomal system, lacquer, patch, bandage, buccal tablet, wafer, sublingual tablet, suppository, vaginal dosage form, or occlusive dressing.

26. The formulation of claim 1, wherein said formulation is in the form of a gel.

27. The formulation of claim 1, wherein said formulation is adapted for transdermal or transmucosal administration according to a schedule having a periodicity selected from once to four times daily dosing.

28. A method for administering diclofenac to a mammal in need thereof, said method comprising transdermally administering to the skin or a mucosal membrane of a mammal a formulation comprising:
   at least 3% wt of diclofenac, C2 to C4 alkanol, polyalcohol, monoalkyl ether of diethylene glycol; and an amount of about 3% wt-5% wt of a fatty alcohol.

29. A method for treating pain; post-traumatic inflammation of tendons, ligaments, muscles, and joints; localized forms of soft-tissue rheumatism; localized forms of degenerative rheumatism; inflammatory disorders; dysmenorrhea; actinic keratosis caused by over-exposure to sunlight; acute migraine; female breast cancer; pain associated with bony metastases; fever due to malignant lymphogranulomatosis (Hodgkin's lymphoma); multi drug resistant *E. coli*; Shy-Drager syndrome; and diabetes mellitus, said method comprising transdermally administering to the skin or a mucosal membrane of a mammal a formulation comprising: at least 3% wt of diclofenac, C2 to C4 alkanol, polyalcohol, monoalkyl ether of diethylene glycol; and an amount of about 3% wt-5% wt of a fatty alcohol.

30. The method according to claim 29, wherein the inflammatory disorder is osteoarthritis.

31. The method according to claim 28, wherein said formulation is administered in combination with another treatment.

32. A kit comprising at least one container comprising a formulation comprising:
   at least 3% wt of diclofenac, C2 to C4 alkanol, polyalcohol, monoalkyl ether of diethylene glycol; and an amount of about 3% wt-5% wt of a fatty alcohol and instructions for use thereof.

33. The kit according to claim 32, wherein said container is adapted for dispensing a predetermined measured amount of said formulation.

* * * * *